(12) United States Patent
Speck

(10) Patent No.: US 9,415,140 B2
(45) Date of Patent: *Aug. 16, 2016

(54) FORMULATIONS FOR DRUG-COATED MEDICAL DEVICES

(71) Applicant: INNORA GMBH, Berlin (DE)

(72) Inventor: Ulrich Speck, Berlin (DE)

(73) Assignee: Innora GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/350,483

(22) PCT Filed: Oct. 11, 2012

(86) PCT No.: PCT/EP2012/070142
§ 371 (c)(1),
(2) Date: Apr. 8, 2014

(87) PCT Pub. No.: WO2013/053809
PCT Pub. Date: Apr. 18, 2013

(65) Prior Publication Data
US 2014/0257181 A1    Sep. 11, 2014

Related U.S. Application Data

(60) Provisional application No. 61/547,448, filed on Oct. 14, 2011.

(51) Int. Cl.
| | | |
|---|---|---|
| *A61F 2/00* | (2006.01) | |
| *A61L 29/16* | (2006.01) | |
| *A61L 31/16* | (2006.01) | |
| *A61L 29/08* | (2006.01) | |
| *A61M 25/10* | (2013.01) | |

(52) U.S. Cl.
CPC .............. *A61L 29/16* (2013.01); *A61L 29/08* (2013.01); *A61L 31/16* (2013.01); *A61M 25/104* (2013.01); *A61L 2300/416* (2013.01); *A61M 2025/1084* (2013.01)

(58) Field of Classification Search
None
See application file for complete search history.

(56) References Cited

U.S. PATENT DOCUMENTS

| | | | | |
|---|---|---|---|---|
| 8,672,990 | B2 * | 3/2014 | Holman et al. | 623/1.11 |
| 9,011,896 | B2 * | 4/2015 | Speck | A61L 29/16 |
| | | | | 424/423 |
| 9,072,812 | B2 * | 7/2015 | Speck | A61L 29/16 |
| 9,078,951 | B2 * | 7/2015 | Speck | A61L 29/16 |
| 9,101,684 | B2 * | 8/2015 | Speck | A61L 29/16 |
| 2004/0230293 | A1 * | 11/2004 | Yip et al. | 623/1.16 |
| 2005/0037048 | A1 | 2/2005 | Song | |
| 2010/0209472 | A1 | 8/2010 | Wang | |
| 2013/0023817 | A1 * | 1/2013 | Speck | A61L 29/16 |
| | | | | 604/22 |

FOREIGN PATENT DOCUMENTS

| | | | |
|---|---|---|---|
| WO | WO 2011/131258 A1 | | 10/2011 |
| WO | WO 2011/131259 | * | 10/2011 |
| WO | WO 2011/131638 | * | 10/2011 |

* cited by examiner

*Primary Examiner* — Dennis J Parad
*Assistant Examiner* — Lyndsey Beckhardt
(74) *Attorney, Agent, or Firm* — Wood, Phillips, Katz, Clark & Mortimer

(57) ABSTRACT

The invention relates to an angioplasty catheter having a balloon and a constraining element carrying at least on a portion of its surface a taxane or taxane preparation and at least one lipophilic antioxidant at a ratio of 3-100% by weight of the at least one antioxidant in relation to 100% by weight of the taxane, wherein a preferred lipophilic antioxidant is propyl gallate. Scoring or cutting balloons as medical devices are excluded.

10 Claims, 2 Drawing Sheets

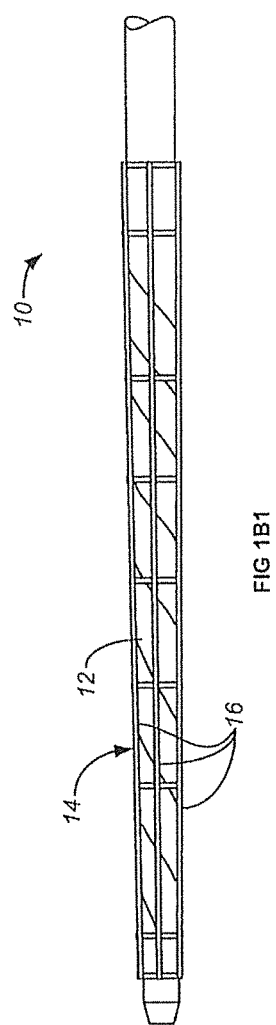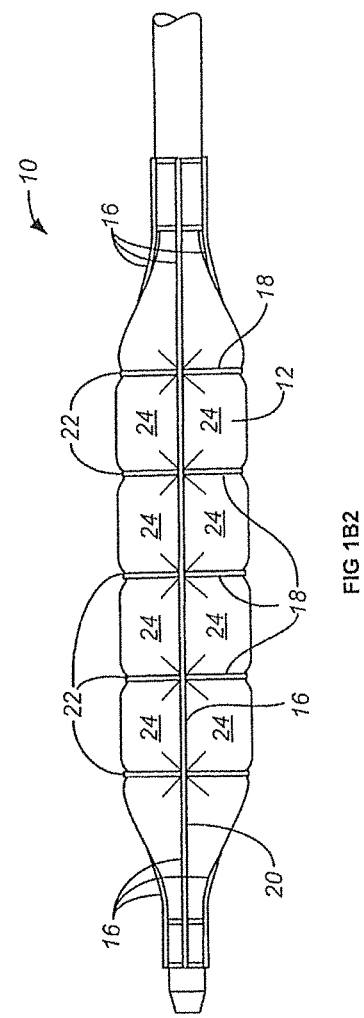

FORMULATIONS FOR DRUG-COATED MEDICAL DEVICES

FIELD OF THE INVENTION

Figure 1A:
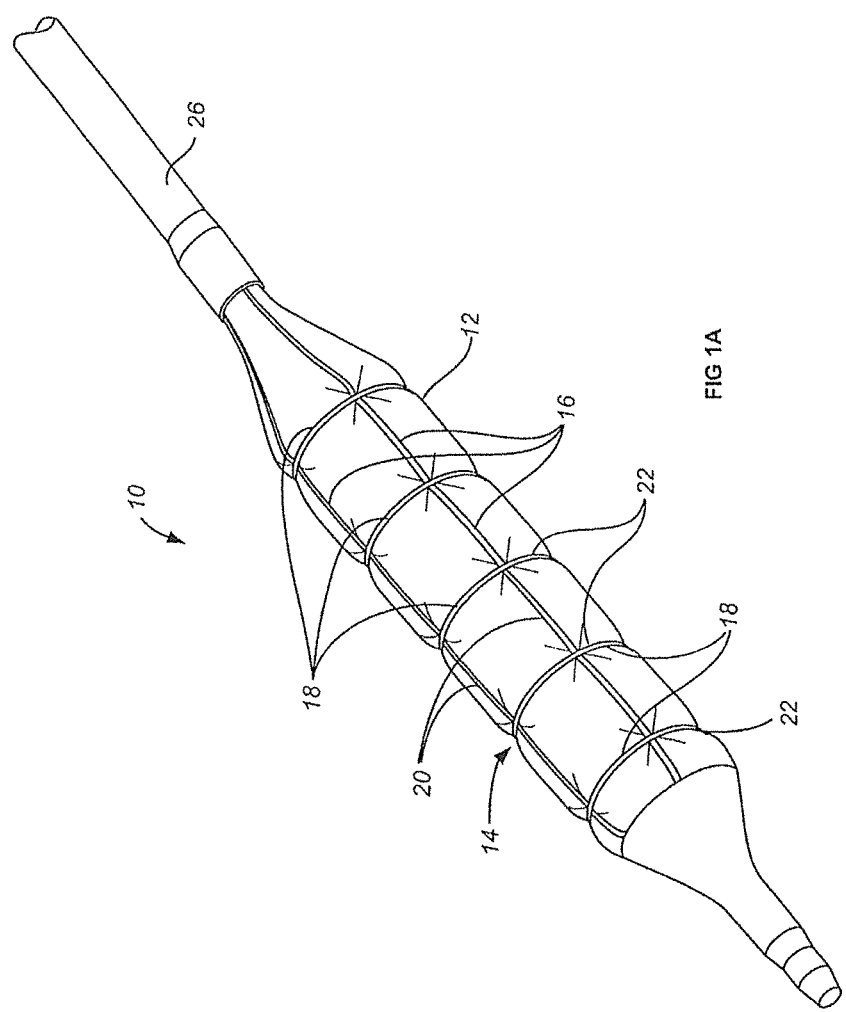

The invention relates to the transfer of a drug loosely adhering to the surface of a medical device to a site inside the body, usually in a diseased blood vessel. The most frequent application is local drug therapy during percutaneous transluminal angioplasty (PTA) or percutaneous transluminal coronary angioplasty (PTCA). These interventions are performed to restore blood flow in stenotic or occluded blood vessels, usually in arteries. A catheter is introduced into a major artery. At the distal end the catheter carries a cylindrical balloon in folded state with very small diameter. In this state the balloon can enter or pass the stenotic or occluded segment of the blood vessel. Once positioned in the narrowed segment, the balloon is inflated with low or high pressure to enlarge the lumen of the blood vessel to its original diameter. Simultaneously, a drug may be transferred to the vessel wall to prevent early and late re-narrowing due to hyperproliferation of the injured vessel wall.

BACKGROUND

Medical devices may contain drugs either to improve the tolerance, efficacy or in vivo life-time of the device or the device serves as carrier for the drug. In any case the dose density (e.g. mg drug/mg device or mg drug/mm$^2$ device surface), chemical stability, adherence, release rate, and total amount released are important and frequently critical features of the drug formulation. These properties are the more critical the more the requirements during production and application of the device vary or may even be contradictory. Drug-coated angioplasty catheters are typical examples: the drug coating must adhere firmly to tolerate mechanical stress during production including folding of balloons, crimping of stents, packaging, transportation to customers, and during final application, which involves passage through a narrow hemostatic valve, an introductory sheath or guiding catheter and a variable distance through possibly tortuous and narrow blood vessels. When the balloon is inflated the drug should be released within a minute or less as rapidly and as completely as possible. The problem was demonstrated by Cremers et al. (Cremers B, Biedermann M, Mahnkopf D, Bohm M, Scheller B. Comparison of two different paclitaxel-coated balloon catheters in the porcine coronary restenosis model. Clin Res Cardiol 2009; 98:325-330) who retrieved as much as 50% of the dose from balloons after expansion for one minute in coronary arteries of pigs, whereas other catheters coated with the same drug and dose but in a different formulation released more than 95%. Almost perfect results (i.e., loss of only 10% of dose and residual drug on the balloon after expansion in an artery of about 10%) were achieved with a rigid prototype balloon (Scheller B, Speck U, Abramjuk C, Bernhardt U, Bohm M, Nickenig G. Paclitaxel balloon coating—a novel method for prevention and therapy of restenosis. Circulation 2004; 110: 810-814). The application of the same coating composition to more flexible modern balloon catheters resulted in problems, i.e., larger premature loss of the drug. All types of balloon catheters display specific challenges in respect of coating the drug on the balloon, sufficient adherence or fast and complete release.

PRIOR ART: PROTECTION FROM PREMATURE DRUG RELEASE

Premature release of a drug from a balloon is a major problem which has been addressed by a variety of methods. Some of them are mechanical, e.g., the use of protection tubes, sleeves, envelops. Examples are U.S. Pat. Nos. 5,370,614, 6,306,166, and 6,616,650 disclosing various protective sheaths which are retracted before the balloon is inflated, or U.S. Pat. No. 6,419,692 proposing a cover which bursts during balloon expansion. A different approach is taken in U.S. Pat. No. 5,893,840 disclosing structured balloon membranes with tiny cavities, WO 94/23787 with roughened balloon membranes to enhance the adherence of coating, or more recently U.S. Pat. No. 7,108,684 proposing a pouch which protects the drug containing layer on the balloon and WO 2009/066330 disclosing methods placing the drug selectively under the folds of a folded balloon. Although efficacious these methods have the disadvantage of increasing the complexity and cost of production or make handling of the devices more difficult or add to the diameter of the devices (which must be kept as small as possible to facilitate passage through stenotic lesions). In some embodiments the protective membranes or perforated membranes prevent a homogeneous transfer of the drug to the tissue or even put the patient at risks.

Other approaches use either physical or chemical methods to control the release of drugs from a balloon surface, e.g., U.S. Pat. No. 5,304,121 describes a hydrogel which releases the drug only after exposure to a triggering agent; U.S. Pat. No. 5,199,951 relies on thermal activation; according to U.S. Pat. No. 7,445,792 a lipophilic 'hydration inhibitor' protects water-soluble drugs from premature release; and according to U.S. Pat. No. 5,370,614 a viscous matrix protects the drug from premature release, however, the viscous matrix must be protected by a sheath during the passage to the stenotic vessel segment. None of the methods has been tested in practice and proven to fulfill the requirements for fast, reliable and complete drug transfer to the target tissue.

The membranes of standard angioplasty balloon catheters consist of polyamide, polyester, polyether, pebax etc. The surface is very smooth with no particular structure. Very little experience exists with structured surfaces. In one case the paclitaxel-coating on a structured surface did not display the desired pharmacological effect because of insufficient drug release in animal experiments (Cremers B, Biedermann M, Mahnkopf D, Böhm M, Scheller B. Comparison of two different paclitaxel-coated balloon catheters in the porcine coronary restenosis model. Clin Res Cardiol. 2009; 98:325-30) and a clinical controlled trial (B Cortese, A. Micheli, A. Picchi, A. Coppolaro, L. Bandinelli, S. Severi, U. Limbruno, Paclitaxel-coated balloon versus drug-eluting stent during PCI of small coronary vessels, a prospective randomised clinical trial. The PICCOLETO Study Heart, 2010, 96, 1291-1296).

Some angioplasty balloons are combined with certain structures made of different material than the balloon membrane, e.g., metal, which is not integrated in and is not part of the balloon membrane. Examples are cutting and scoring balloons and a recently developed balloon which is surrounded by constraining elements which expand during inflation with the balloon (WO 2011/112863 A1). The option to coat the balloon with certain drugs directly or using a matrix or microcapsules is mentioned in WO 2011/112863 A1 (see paragraphs [0015, 0035, 0038]. Drug coating of these more complex devices requires specific methods and compositions. The coating must be introduced at the appropriate stage of production, e.g. before the additional structures are mounted on the balloon or thereafter. Adherence, release and the chemical stability of the coating are affected differently by different material. Adherence and release depend on the geometrical structure and the relative movements of the folds and constraining elements to each other. All these properties normally vary greatly if a combination of different materials has to be coated.

Numerous methods of sustained drug release are known and successfully used in practice but are not applicable to medical devices which are in contact with the target tissue only a few seconds or minutes. Sustained drug release is usually achieved by embedding the drug in a polymer which restricts the diffusion rate to the surface and in this way controls the transfer into the adjacent tissue.

Therefore, a need remains for a method or formulation which protects the coating from premature losses during production, handling, and on the way to the lesion and still allows the immediate and complete release of the active ingredient at a location and point in time determined by the user.

An advantageous way to control adherence and release of a drug from a medical device, e.g., an angioplasty balloon, is the selection of a suitable formulation and coating which do not require mechanical protection, or additional physical or chemical interaction with the coating except the usual operation of the device, e.g., inflation of a folded balloon to induce the release of the drug. Although desirable and frequently tried, the conflicting objectives of perfect adherence before use and immediate release at the site of action make it a difficult task. A large variety of patent applications vaguely disclose measures, compositions and devices to solve this problem either by the selection of drugs, the choice of specific coating processes or formulations containing various additives. Long lists of compounds have been copied from textbooks of chemistry, pharmacology, or pharmacy but even with extensive experimentation disclosures are not sufficiently clear to allow a person familiar with the subject and skilled in the art to come to a satisfactory solution without an inventive step. Examples of prior art are US 2008/0118544 reciting an excessive number of substances and substance classes or U.S. Pat. No. 7,445,795 which discloses the use of 'hydration inhibitors' not applicable to the preferred class of very lipophilic drugs which require 'hydration enhancers' or 'dispersion and dissolution enhancers' as, e.g., disclosed in WO 2004/028582. Although the hydrophilic additives (which may be regarded as 'hydration enhancers') work quite well on certain balloon membranes (Scheller B, Speck U, Abramjuk C, Bernhardt U, Bohm M, Nickenig G. Paclitaxel balloon coating—a novel method for prevention and therapy of restenosis. Circulation 2004; 110: 810-814) the adherence of the drug admixed to these excipients to various modern PTA or PTCA balloons is either too weak or too tight resulting in premature loss of a major proportion of the drug or incomplete release at the target site.

PRIOR ART: ANTIOXIDANTS

In theory, antioxidants address an almost universal feature of diseased tissue, namely the 'reactive oxygen species', and should have widespread medical applications. In practice, only very few controlled clinical trials have shown beneficial effects of antioxidants (Suzuki K. Antioxidants for therapeutic use: Why are only a few drugs in clinical use? Advanced Drug Delivery Reviews 2009; 61:287-289). Antioxidants are mentioned as potentially useful drugs for the treatment of focal vascular disease such as stenosis, restenosis, atherosclerotic plaques, and vulnerable plaques in US 2009/0136560 with no additive, in U.S. Pat. No. 5,571,523 as agents inducing apoptosis in vascular smooth muscle cells, in WO 2004/022124 either as active drugs or as 'hydration inhibitors'. In US 2008/0241215 probucol, a drug approved for the treatment of hyperlipidemia, a known risk factor for atherosclerosis, is proposed as the active ingredient in stent coating, either alone or combined with rapamycin or another antirestenotic agent in a slow-release formulation. U.S. Pat. No. 6,211,247 claims pharmaceutical compositions containing an effective dose of resveratrol for preventing or treating various vascular pathologies following coronary interventions. Similarly, US 2007/0037739 discloses local delivery systems comprising various bioactive agents including resveratrol which either alone or in the specified combinations are suitable for treating or preventing abnormal luminal cell proliferation. None of the above-mentioned documents contains data encouraging the use as additives to a lipophilic drug to delay the release rate of the drug and no specific compositions are disclosed which address the above-mentioned problems of adhesion of a drug before the target lesion is reached and immediate release when required.

Small proportions of antioxidants are commonly used to protect drugs or nutrients from decomposition by oxygen or oxidation, an application which has also been proposed for drugs coated on implantable medical devices such as stents (US 2007/0020380, US 2009/0246253) or balloon catheters (US 2005/0037048, US 2009/0246252, especially paragraph [105] However, antioxidants are commonly used in proportions of less than 1% by weight in relation to 100% by weight of the drug. Normally it is intended to use as less antioxidant as possible, i.e., less than 0.1% by weight in relation to 100% by weight of the drug (Voigt R. Lehrbuch der pharmazeutischen Technologie. 5. Edition, Verlag Chemie, Weinheim—Deerfield Beach, Fla.—Basel, 1984). US 2005/0037048 discloses a specific example which refers to a selected drug in a polymeric matrix requiring an unusually high proportion of antioxidants.

Again, none of the above mentioned documents provides any hint to an advantage in using antioxidants in combination with stable (i.e. oxidation-resistant drugs) and/or at dose levels which provide no therapeutic or prophylactic action.

PRESENT INVENTION

The problem underlying the present invention was the provision of a medical device with an improved adherence of the drug without negative effect on the release of the drug at the target site. Especially, the problem underlying the present invention was the provision of a medical device for short lasting use, e.g. angioplasty, consisting of different materials, with an improved adherence of the drug without negative effect on the release of the drug at the target site.

The problem was solved by a medical device according to claim 1. In other words, the problem was solved by a medical device carrying at least on a portion of its surface at least one oxidation-insensitive drug or oxidation insensitive polymer-free drug preparation and at least one lipophilic antioxidant at a ratio of 3-100% by weight of the at least one antioxidant in relation to 100% by weight of the drug, wherein the at least one oxidation-insensitive drug is a taxane, preferably paclitaxel, and the at least one lipophilic antioxidant is selected of nordihydroguaiaretic acid, resveratrol, propyl gallate, preferably propyl gallate, and wherein scoring or cutting balloons as medical devices are excluded. "Polymer-free" means that no additional polymer is part of the coating. Preferred embodiments are disclosed in the dependant claims. Usually, antioxidants are used to stabilize oxidation-sensitive drugs against degradation by oxygen. They are considered useless in this regard if the drug is stable against oxidative degradation, i.e. if the drug is oxidation-insensitive. Below, the terms "oxidationinsensitive drug", "active drug" and "drug" are used interchangeable all meaning an oxidation-insensitive drug if the invention is concerned.

During testing of a large variety of coating methods, additives and drug combinations the surprising discovery was made that certain lipophilic antioxidants added to less or even more lipophilic and more or less water-soluble drugs, which are oxidation-insensitive, such as inhibitors of cell proliferation or inhibitors of the formation of neovasculature in a defined mass ratio significantly increase the adherence of the drug to a variety of state-of-the art balloon membranes during handling and on the way to the target lesion even if the target lesion is located far away from the site where the device first enters a blood-filled introductory sheath, guiding catheter or vessel containing rapidly flowing blood. Thus, at least one lipophilic anti-oxidant in an amount of 3-100% by weight is used as an adherence improver for drugs coated on a medical device during this initial step of introducing the medical device into the vasculature. The wording "at least one lipophilic antioxidant" includes single antioxidants but also mixtures of different antioxidants. Other substances or pharmaceutical compounds may be added to further adjust the properties of the product to the demand in respect of stability or other pharmaceutical requirements and tolerance etc.

Scoring or cutting balloon catheters are explicitly excluded as medical devices.

Examples of active drugs are inhibitors of cell proliferation such as taxanes, preferably paclitaxel, docetaxel and protaxel. These drugs may be combined with other drugs if different pharmacological actions or release profiles are required or efficacy or tolerance is to be improved. Thus, the wording "at least one drug or drug preparation" means that single drugs but also mixtures of different drugs are included. Preferred drugs are either lipophilic (partition coefficient between n-butanol and water>10, or display very poor water solubility (<1mg/ml, 20° C.). Preferred are those drugs which in dry state are chemically stable during long-term storage without the addition of an antioxidant, e.g., paclitaxel and other taxanes. Thereof, the preferred ones are paclitaxel, protaxel and docetaxel with paclitaxel being the most preferred drug. Drugs must be used in a dose range providing the desired effect without compromising the technical features of the coated balloon such as flexibility. A preferred dose range is between 1 and 10 µg/mm² balloon surface, most preferred up to 6 µg/mm². The lipophilic antioxidants are solid at temperatures up to 40° C. A preferred antioxidant is propyl gallate. As explained above, the wording "at least one drug or drug preparation" means single drugs but also mixtures of different drugs and the wording "at least one lipophilic antioxidant" includes single antioxidants but also mixtures of different antioxidants.

Combinations of the preferred antioxidant with the above-mentioned drugs showed an improved adherence. Different combinations, especially with other oxidation-insensitive drugs, did not show a significantly improved adherence or required very high amounts of the antioxidant which impairs the mechanical features of the balloons (much more than 100% by weight in relation to 100% by weight of the drug) or did not provide the desired pharmacologic effect.

Lipophilic antioxidant means that the partition coefficient of the antioxidant between n-butanol and water is >1, more preferred >10 and even more preferred >100.

Preferably, the drug is more lipophilic than the antioxidant, i.e., the partition coefficient between n-butanol and water of the drug is higher than the partition coefficient between n-butanol and water of the antioxidant. If, however, an excipient prevents premature loss of the drug from the medical device and/or enhances the fast and complete transfer to the tissue it shall not be excluded because of its physicochemical properties.

At the dose density used the chosen antioxidant does not display relevant therapeutic or prophylactic effects in respect of the disease which is treated by the coated medical device nor is the relative amount of the antioxidant chosen to protect the drug from oxidative decomposition. This means that a non-bioactive dose of the antioxidant is preferred. The dose density and the mass relation of the antioxidant to the drug are solely optimized in respect of adherence of the drug to and release from the medical device surface. The antioxidant dose on the medical device is too low to provide the desired pharmacological effect, i.e., it is ineffective on its own. The antioxidant on the medical device is not required to protect the active drug (e.g., the antiproliferative or immunosuppressive drug) from oxidative decomposition during production, sterilization and storage; at least it is not required at the dose or concentration applied according to this invention. 'Not required' means that the active drug is stable enough without the antioxidant or at an antioxidant dose or dose density or ratio to the active drug below the dose according to the present invention. 'Sufficient stability' means that less than 5% of the active drug is lost due to oxidative decomposition between the coating of the device and the use in patients one year after production if stored at ambient temperature (=drug or drug preparation stable against oxidative decomposition, air-oxygen exposure not excluded). In conclusion the invention relates to a combination of an antioxidant with a drug which needs no protection from oxidative decomposition or at least a dose of the antioxidant which surpasses the amount of antioxidant required protecting the drug from oxidation by its antioxidant action. The antioxidant serves as additive or excipient not functioning as a stabilizer for an oxidation-sensitive biologically active ingredient (drug) nor displaying a therapeutic or pro-phylactic effect on its own at the selected dose.

The dose of the antioxidant on the surface of a medical device may be defined in respect of the therapeutic drug. Preferred relationships (weight/weight) are 3-100% antioxidant of the weight of the drug. For example, if the dose density of the drug is 5 µg/mm² device surface, the amount of antioxidant is 0.15-5.0 µg/mm². Higher proportions of the antioxidant may be selected if either the drug is applied at a dose below 3 µg/mm² device surface or the adherence of the drug to the device surface is further improved. The antioxidant load of the device may reach 10 µg/mm². A higher load is possible. Other preferred ranges for the relationship of antioxidant to drug on a weight/weight basis are 5-100%, more preferred 10-100%, and even more preferred 20-100% and most preferred 50-100% in relation to 100% of the drug. Especially the range of 50-100% on a weight/weight basis enhances the adherence significantly. Lower amounts improve the adherence correspondently less, i.e. the more antioxidant the better is the adherence showing a correlation in the preferred range. However, more than 50% improve the adherence more than would be expected considering a linear correlation. The relationship may also be defined in respect of moles: in a preferred embodiment the antioxidant is present from 10 mole % relative to the drug to 200 mole %. Higher amounts of the antioxidant may be useful; they may be only excluded if they display on their own significant pharmacological prophylactic or therapeutic effects in respect of the disease to be treated.

If more than one drug is used the total weight of the drugs or the total moles of the drugs serve as basis for the calculation of the amount of the antioxidant. If more than one antioxidant is used the total weight of the antioxidants or the total moles of the antioxidants serve as basis for the calculation of the amount of the antioxidants.

Other well tolerated and approved additives and/or excipients may be applied to further improve the mechanical or pharmaceutical properties of the coating. Polymer-free coating compositions are preferred. It is a special advantage of the present compositions that they do not require the use of polymers to prevent premature release of the drug. Nevertheless, small amounts of pharmaceutically acceptable polymers such as polyacrylic acids may be added, e.g., to improve the distribution of the drug on the balloon or adherence of the dry coating during handling. Small amounts mean about 1-20% by weight in relation to 100% by weight of the drug(s). If polymers are used substances with low to moderate molecular weight, i.e., 2000 to 50 000 D are preferred.

Usually, drugs and mixtures of drugs with additives are coated on medical devices as liquid formulations in volatile solvents, according to the current invention preferably without addition of a polymer, i.e. polymer-free. The choice of solvent is important for the structure of the coating in dry state and the adherence and release of the drug from the surface. Preferred organic solvents are acetone, tetrahydrofuran, and various alcohols such as methanol, ethanol, and isopropyl alcohol (isopropanol). Usually, 1 to 30% (volume/volume) water is added. The drug or drugs and the antioxidant may be applied at the same time dissolved in the same solvent or mixture of solvents. Alternatively, they may be separately dissolved in the same or different solvents and sequentially applied. The solution(s) is/are polymer-free in either case. In a preferred embodiment, the medical device has been polymer-free coated with at least one oxidation-insensitive drug and at least one lipophilic antioxidant both dissolved in tetrahydrofuran or a mixture of solvents containing more than 25% (v/v) tetrahydrofuran or each separately dissolved optionally selecting a different solvent for the at least one lipophilic antioxidant. Another preferred embodiment is based on a medical device, which has been polymer-free coated with at least one oxidation-insensitive drug and at least one lipophilic antioxidant both together dissolved in acetone or a mixture of solvents containing more than 25% (v/v) acetone or each separately dissolved optionally selecting a different solvent for the at least one lipophilic antioxidant. Yet another preferred embodiment is a medical device, which has been coated with at least one drug and at least one lipophilic antioxidant both together dissolved in isopropanol or a mixture of solvents containing more than 25% (v/v) isopropanol or each separately dissolved optionally selecting a different solvent for the at least one lipophilic antioxidant. Coating with dry particles such as micro- or nanoparticles, crystals, capsules etc. or particles suspended in a liquid preparation is possible. Coating with particles may be facilitated by a roughened or sticky surface of the medical device.

A variety of coating procedures providing more or less uniform layers on medical devices are known from the literature and are disclosed in patent applications. These include simple dipping, spraying, and methods providing precise doses and homogeneous distributions (e.g., WO 2009/018816). Coating may be applied stepwise, either as multiple layers of the same composition or as layers with different compositions e.g. the drug first and the antioxidant second or in the opposite order. All these methods may be applied to the formulations of the current invention. The sequential coating with, e.g., (a) the drug first and (b) second the antioxidant dissolved in a solvent in which the drug is poorly soluble by, e.g., spraying results in substantially separate layers. This is completely different from the application of antioxidants for chemical protection of oxidation sensitive drugs which requires a homogeneous mixing of the antioxidant with the drug. Thus, a preferred embodiment is a medical device, which has been sequentially coated polymer-free with at least one oxidation-insensitive drug and at least one lipophilic antioxidant in a way that the drug and the antioxidant are not homogeneously mixed.

Furthermore, coated medical devices may be dried under different conditions such as temperature, air flow, gas composition, and pressure at different stages of the production process. They may be stored in water-vapor-tight seals with a separately packed water-absorbing agent within the seal.

Preferred medical devices are balloon catheters, e.g., catheters for angioplasty or coronary angioplasty except scoring or cutting balloon catheters. Most preferred medical devices are balloon catheters for short-lasting use during an interventional image guided therapy. Short lasting use means that the device is not implanted but eliminated from the body when the procedure is finished, usually within less than 10 minutes, but never later than a few, preferably 5, hours after the end of the procedure. Catheters may contain balloon membranes made from various polymers and copolymers, polyamides (nylon 12, pebax), polyethylenes, polyurethanes, latex, ChronoPrene™, silicone, various polyvinyls and the like.

Independently of the type of material, the adherence and release properties of drugs are improved by the addition of the selected lipophilic antioxidants.

The medical device carries the at least one drug or drug preparation and the at least one lipophilic antioxidant at least on a portion of its surface which is aimed at coming into close contact with the tissue to be treated, e.g., a balloon at the distal portion of a catheter shaft. This means that at least 5%, preferably more than 50%, most preferably more than 90% of the surface is coated. Preferably, the coating is present at least on the surface of the device where it has the widest diameter. If less than 100% of the device's surface is coated, preferably the parts starting with the lowest device diameter are omitted. However, parts such as holds/handles or shafts are omitted per se. A balloon as part of a balloon catheter, which is a preferred medical device, has a central cylindrical part and two opposite conical ends. If less than 100% of the balloon catheter's surface is coated, it is preferred that the cylindrical part is coated and that at least parts of or the complete conical ends remain uncoated.

Another embodiment is a balloon with a constraining structure as described in WO 2011/112863 A1. The balloon differs from conventional angioplasty catheters in that it contains a constraining structure, e.g., metal wires tightly surrounding the folded balloon. The wires are not folded in the same way as the balloon but are exclusively located on its external surface. Such balloon with external constraint structure is already known from WO 2011/112863 A1. The full disclosure of which is incorporated herein by reference.

In brief, a preferred balloon catheter is designed to modulate the inflation characteristics of the balloon to provide a segmented compartmental dilatation with local regions of compliance capable of conforming to the uneven nature of the vascular disease. It includes a constraining structure (CS). The CS serves to control and limit balloon inflation and modify balloon topography, typically by forming protruding regions ("pillows") over the surface that cause local dilatation in a small region of the vessel independent of those formed by neighboring protruding regions. Such discrete protruding regions will each separately engage a segment of the lesion when the balloon is inflated so that the pressure and degree of balloon expansion applied against that segment is controlled and limited, thus reducing the risk of trauma while assuring that all segments of the lesion are adequately treated.

The constraining structure may have a non-expanded configuration where it lies closely over folds of the balloon prior to inflation and an expanded configuration which is smaller than an unconstrained size of the balloon (when fully inflated) so that the structure restrains the balloon inflation along a plurality of crossing channel lines. By "crossing" channel lines, it is meant that the channels will intersect at a plurality of locations so that the channels comprise an intersecting matrix of interconnected channels. Individual channel lines may be oriented axially, circumferentially, or preferably will include channel lines with both axial and circumferential orientations where the axial channels intersect the circumferential channels. Alternatively, the channels could be formed as two or more counter wound helical channels that intersect to form diamond-shaped protruding regions.

In specific preferred embodiments, the constraining structure comprises a plurality of circumferentially spaced-apart axial struts and a multiplicity of axially spaced-apart radially expandable rings attached to the axial struts. The rings are joined to the struts at intersecting angles, preferably in the range from about 75° to 105°. In particularly preferred embodiments, the intersecting angles will be 90°. The axial struts will be coupled to the catheter on both a distal side of the balloon and on a proximal side of the balloon. In some embodiments, at least one of the distal strut ends and the proximal strut ends will be free to translate axially over the catheter shaft as the balloon is inflated (to accommodate foreshortening which would otherwise occur). Alternatively, the individual struts may be fixedly attached to the catheter shaft on both the proximal and distal side of the balloon where the struts are elastic or otherwise stretchable in tension so that they will elongate as the balloon is inflated. For example, axial struts could be composed of an elastomer or other elastic material which allows elongation. More typically, the axial struts would include features, such as zig-zags, S-shaped links, coil springs, or the like, which would accommodate elongation (if needed) when either or both of the strut ends are attached to the catheter shaft.

The radially expandable rings will also be formed so that they can stretch or elongate to increase in diameter as the balloon is inflated in the ring. The expandable rings could be formed from inherently elastic materials, such as stretchable polymers or the like, but more typically will be formed with expansible features which allow the ring to expand when the balloon is inflated. The expandable features can be the same as with the axial struts, including zig-zags, S-shaped curves, coils, and the like. In all cases, it is necessary that the rings have a maximum diameter beyond which they will not further increase in size as the balloon is inflated. When the rings are formed with expandable features, the maximum ring expansion will occur when these features are fully elongated. If an elastomeric or other material is used to form the rings, non-distensible tethers or other expansion limits can be built into the rings so that they do not exceed their desired maximum diameter. The constraining structure and its position relative to the balloon membrane are defined by the function to constrain the expansion of a more or less compliant membrane. The constraining structure may cover the folds, the balloon surface, be part of the balloon membrane or may adhere to the inner surface of the balloon membrane.

FIGS. 1A, 1B2 and 1B2, which are identical to FIGS. 2A, 2B1 and 2B2 of WO 2011/112863 A1, show a constraining structure located on a balloon prior to inflation (FIG. 1B1) and after inflation (FIGS. 1A and 1B2).

FIGS. 1A, 1B1 and 1B2 show an exemplary constraining structure 14 in accordance with WO 2011/112863 A1, which comprises a plurality of axial struts 16 and axially spaced-apart radially expandable rings 18. When the balloon 12 and the catheter 10 is in its non-inflated state (as illustrated in FIG. 1B1), the balloon is folded with a number of overlapping lobes. The constraining structure 14 has a generally cylindrical geometry with a diameter just large enough to cover the deflated balloon 12.

As the balloon 12 is inflated, as illustrated in FIGS. 1A and 1B2, the radially expandable rings 18 expand in response to the force of the balloon. The rings will be structured, however, so that they reach a maximum diameter beyond which they will no longer radially expand regardless of the continued inflation or expansion of the balloon. As the axial struts 16 are attached or otherwise coupled to the radially expandable rings 18, the radially outward travel of the struts is also limited to a distance defined by the maximum diameter of the rings. Thus, as the balloon will have a fully inflated diameter which is larger than that of the maximum diameter of the radially expandable rings 18, when the balloon is fully inflated a plurality of axial and circumferential channels 20 and 22, respectively, will be formed in the balloon surface. A plurality of protruding regions 24 (as seen in FIG. 1B2) are defined in the openings or in interstices between the adjacent axial struts 16 and radially expandable rings 18.

It was found that certain coating compositions and coating methods mentioned above are particularly suitable to coat these balloons in spite of the more complicated construction of the catheter. One of the problems is that balloons cannot be folded in the proper way after the constraining elements have been mounted. If coating is performed with the compositions disclosed in the following paragraph on the expanded or folded balloons before mounting the constraining elements a very low loss of this coating is observed. In spite of the fact that the wires are not coated transfer of the drug to the vessel wall is surprisingly homogeneous. Coating of the final product (with the constraining element on the folded balloon) is also possible. A sufficiently homogeneous coating depends on the appropriate combination of solvents, excipients and drugs.

Examples of suitable coating compositions are combinations of paclitaxel and propyl gallate.

Preferred examples of suitable coating compositions are combinations of paclitaxel and propyl gallate in acetone, isopropanol, ethanol and water or mixtures thereof. If paclitaxel is chosen as the active ingredient and propyl gallate as excipient a ratio of 10:0.5 to 10:10 (w/w) is preferred, 10:1 to 10:5 is more preferred and 10:2-10:5 is the most preferred composition. If more than one excipient is used on the same balloon then the ratio between drug and excipients applies to the sum of excipients. Some of the most preferred compositions are described in examples 4.

Below, the invention is described by means of Examples.

EXAMPLES

Example 1

Balloons for percutaneous transluminal angioplasty according to WO 2011/112863 A1, FIGS. 2A-2B2 (here FIGS. 1A-1B2) were coated in a folded stage with pre-mounted constriction elements either with paclitaxel alone or with paclitaxel and propyl gallate (PG); the coated balloons (dry, ready for use) were exposed to mechanical stress or passed through a hemostatic valve, blood filled guiding catheter and floated in blood; loss of the drug from the balloons coated with paclitaxel only set=100. The results are shown in Table 1. Propyl gallate reduced the loss after mechanical stress by more than 50% and the loss during the passage through a valve and guiding catheter by almost 3 quarters.

TABLE 1

| Coating solution | Loss due to mechanical stress | Loss during the passage through the valve, guiding catheter and blood |
| --- | --- | --- |
| Paclitaxel in acetone/ethanol/H$_2$O | 100 | 100 |
| Propyl gallate 48% = 0.48 mg PG/mg paclitaxel acetone/ethanol/H$_2$O | 41.6 ± 6.2 | 26.7 ± 21.5 |

Example 2

Balloons for percutaneous transluminal angioplasty according to WO 2011/112863 A1, FIGS. 2A-2B2 (here FIGS. 1A-1B2) were coated in a folded stage with premounted constriction elements either with paclitaxel and propyl gallate (PG) or butylated hydroxy toluene (BHT). Coated balloons were tested in respect of homogeneity of the distribution of the coating on the expanded balloons, paclitaxel loss during the passage through a hemostatic valve, a Medtronic Launcher JL 3.5 6F guiding catheter and in stirred blood (37° C.) for one minute, and the drug release during angioplasty. The results are shown in Table 2. Coating of the balloons with premounted constriction elements was surprisingly successful. In spite of the heterogeneity of the structure with folds and wires the coating was almost or perfectly homogeneous, the loss of drug on the way to the lesion was minimal and the release during only one minute inflation in a coronary artery of a swine almost complete. Example 2 indicates that the improved adherence of the formulation with propyl gallate shown in example 1 is not achieved at the expense of reduced release at the target site.

TABLE 2

| Coating solution | Stability during sterilization and storage | Distribution on expanded balloons | Loss on the way to the lesion % of dose | Released during angioplasty % of dose |
| --- | --- | --- | --- | --- |
| Propyl gallate 48% = 0.48 mg PG/mg paclitaxel acetone/ethanol/H$_2$O | stable | largely homogeneous | 1 ± 15 | 82 ± 2 |
| Propyl gallate 24% = 0.24 mg PG/mg paclitaxel THF/ethanol/H$_2$O | stable | homogeneous | 6 ± 9 | 84 ± 2 |
| BHT 12% = 0.12 mg BHT/mg paclitaxel acetone/ethanol/H$_2$O | >50% of BHT evaporates | homogeneous only in longitudinal direction | 12 ± 7 | 89 ± 4 |

The invention claimed is:

1. An angioplasty balloon catheter characterized by a catheter shaft having an inflatable balloon at its distal end and a constraining structure constraining the expansion of the inflatable balloon, said constraining structure having a non-expanded configuration prior to inflation and an expanded configuration which is smaller than an unconstrained size of the balloon so that the structure restrains the balloon inflation along a plurality of crossing channel lines, carrying at least on a portion of said balloon's surface: a) paclitaxel or a polymer-free paclitaxel preparation; and b) at least one lipophilic antioxidant at a ratio of 3-100% by weight of the at least one antioxidant in relation to 100% by weight of the paclitaxel, wherein the at least one lipophilic antioxidant is selected of propyl gallate, nordihydroguaiarectic acid, or resveratrol, wherein scoring or cutting balloons as medical devices are excluded.

2. The angioplasty balloon catheter as in claim 1, wherein the constraining structure comprises a plurality of circumferentially spaced-apart axial struts and a multiplicity of axially spaced-apart radially expandable rings attached to the axial struts, wherein the axial struts cross the radially expandable rings.

3. The angioplasty balloon catheter as in claim 2, wherein the individual struts are each elastic in tension so that they will elongate as the balloon is inflated.

4. The angioplasty balloon catheter according to claim 1, wherein the lipophilic antioxidant is propyl gallate.

5. The angioplasty balloon catheter according to claims 1 or 4, wherein the at least one lipophilic antioxidant is contained at a ratio of 5-100% by weight of the at least one lipophilic antioxidant in relation to 100% by weight of the paclitaxel.

6. The angioplasty balloon catheter according to claim 1 or 4, wherein the antioxidant load is up to 10 µg/mm$^2$ of coated device surface.

7. The angioplasty balloon catheter according to claim 1, which has been sequentially coated polymer-free with the paclitaxel and at least one lipophilic antioxidant in a way that the paclitaxel and the antioxidant are not homogeneously mixed.

8. The angioplasty balloon catheter according to claim 5, wherein the at least one lipophilic antioxidant is contained at a ratio of 10-100% by weight in relation to 100% by weight of the paclitaxel.

9. The angioplasty balloon catheter according to claim 5, wherein the at least one lipophilic antioxidant is contained at a ratio of 20-100% by weight in relation to 100% by weight of the paclitaxel.

10. The angioplasty balloon catheter according to claim 5, wherein the at least one lipophilic antioxidant is contained at a ratio of 50-100% by weight in relation to 100% by weight of the paclitaxel.

* * * * *